(12) United States Patent
Clapham

(10) Patent No.: US 6,245,059 B1
(45) Date of Patent: Jun. 12, 2001

(54) OFFSET ABLATION PROFILES FOR TREATMENT OF IRREGULAR ASTIGMATION

(75) Inventor: Terrance N. Clapham, Jamestown, CA (US)

(73) Assignee: VISX, Incorporated, Santa Clara, CA (US)

(*) Notice: Subject to any disclaimer, the term of this patent is extended or adjusted under 35 U.S.C. 154(b) by 0 days.

(21) Appl. No.: 09/287,322

(22) Filed: Apr. 7, 1999

(51) Int. Cl.$^7$ ....................................... A61B 18/18
(52) U.S. Cl. ..................... 606/5; 606/4; 606/10; 606/13; 128/898
(58) Field of Search ............... 606/4–6, 10–16, 606/166

(56) References Cited

U.S. PATENT DOCUMENTS

| | | |
|---|---|---|
| 4,724,522 | 2/1988 | Belgorod . |
| 5,098,426 | 3/1992 | Sklar et al. . |
| 5,290,272 | 3/1994 | Burstein et al. . |
| 5,314,422 | 5/1994 | Nizzola . |
| 5,391,165 | 2/1995 | Fountain et al. . |
| 5,437,658 * | 8/1995 | Muller et al. ............................ 606/5 |
| 5,439,462 | 8/1995 | Bille et al. . |
| 5,549,596 | 8/1996 | Latina . |
| 5,549,597 | 8/1996 | Shimmick et al. . |
| 5,556,395 | 9/1996 | Shimmick et al. . |
| 5,634,919 | 6/1997 | Azar . |
| 5,637,109 | 6/1997 | Sumiya . |
| 5,683,379 | 11/1997 | Hohla . |
| 5,752,967 * | 5/1998 | Kritzinger et al. .................. 606/166 |
| 5,779,696 * | 7/1998 | Berry et al. ............................ 606/16 |
| 5,984,916 * | 11/1999 | Lai ........................................ 606/11 |

* cited by examiner

*Primary Examiner*—John P. Leubecker
*Assistant Examiner*—Agned Farah
(74) *Attorney, Agent, or Firm*—Townsend Townsend & Crew LLP; Mark D. Barrish, Esq.

(57) ABSTRACT

The invention provides near-term customized ablation capabilities for treatment of corneal irregularities by ablating laterally offset refractive therapy profiles. These treatment profiles may, when centered on the eye, be suitable for treatment of standard refractive errors such as myopia, hyperopia, and cylindrical astigmatism. By selectively offsetting one or more of these ablation profiles at selected points across the corneal surface, the laser system can reduce refractive errors resulting from corneal irregularities such as irregular astigmatism, corneal steepening in one quadrant, asymmetrical astigmatism, irregularities inadvertently produced by a prior refractive treatment (such as radial keratotomy incisions, a decentered ablation, or the like), granular dystrophy, diffuse, asymmetric warpage as a result of post-corneal transplants, bilateral keratoconus, penetrating keratoplasty, or the like.

11 Claims, 11 Drawing Sheets

| Ablation Type | | Parameters | |
| --- | --- | --- | --- |
| | | Minimum | Maximum |
| Myopic Surfaces | | | |
| Sphere | | 0 D | -30.0 D |
| | Diameter | 1.2 mm | 6.5 mm |
| Cylinder | | 0 D | -15.0 D |
| | Length | 4 mm | 6.5 mm |
| | Width | 3.0 mm | 6.5 mm |
| | Transition zone | 0.2 mm | 0.6 mm |
| Ellipse | | 0 D | -30.0 DS, -15.0 DC |
| | Major Axis | 2.5 mm | 6.5 mm |
| Hyperopic Surfaces | | | |
| Sphere | | 0 D | +6.0 D |
| Cylinder | | 0 D | +4.0 D |
| | Outer Diameter | 6.0 mm | 9.0 mm |
| | Inner Diameter | 3.0 mm | 6.0 mm |
| Transition Zone (outer-inner) | | 3.0 mm | 4.5 mm |
| Therapeutic Surfaces | | | |
| PTK Slit | Length/Width | 0.6 mm | 6.0 mm |
| PTK Circle | Diameter | 2.0 mm | 6.0 mm |
| | Transition Zone | 0 | 2.7 mm |

| Last name: | Smith | | First name: | John | | | |
|---|---|---|---|---|---|---|---|
| ID: | 261324 | | Eye: | OS ▸ | | | |

Patient Info | Preop Exam | Refractive | Op Params | Notes

Contoured Ablation Patterns

| | Sphere | Cyl | Axis | Size | Offsets | Surface | APA/Mrg/Pse |
|---|---|---|---|---|---|---|---|
| 1. | -14.25 D S | | | 2.0 mm | -1.7, 2.2 | M Sphere | APA |
| 2. | -24.00 D S | | | 1.5 mm | 2.2, 2.3 | M Sphere | APA |
| 3. | -24.00 D S | | | 1.2 mm | -1.9, -2.6 | M Sphere | APA |
| 4. | -15.00 D S | | | 2.0 mm | 2.6, -2.7 | M Sphere | APA |

Vertex: 12.50 mm

Keratometer K1: 43.50 D   K2: 43.50 D   K2 Axis: ▢

☐ Adjust for LASIK by -7%

Select Treatment

Results

Pulse rate: (open) 6.5 Hz                    Pulses: 251

[Treat] [Summary] [Print] [Elect]

FIG. 11B.

Myopic Spherical Surface Entry

Desired correction: -14.25 DS     Diameter: 2.0 mm ← 82

Offsetsss: X: -1.7 mm   Y: 2.2 mm   Depth: 19.12 um
   ↑
   80

☐ Pause After Surface
☐ Merge with following sphere
☑ APA
↑
84

[Ok]   [Cancel]

OFFSET ABLATION PROFILES FOR TREATMENT OF IRREGULAR ASTIGMATION

BACKGROUND OF THE INVENTION

1. Field of the Invention

This invention generally relates to laser eye surgery, and in particular, provides methods, devices, and systems for selectively ablating corneal tissue to improve the vision of patients having corneal irregularities.

Laser eye surgery systems and methods are now used to correct defects in vision using a technique known as ablative photodecomposition. In general, these techniques selectively expose the cornea to laser radiation so as to selectively remove and resculpt the cornea and achieve a desired change in shape of the cornea to treat an optical defect.

Laser eye surgery is now being used to treat a variety of vision defects, including myopia (nearsightedness), hyperopia (farsightedness), and symmetrical cylindrical astigmatisms. To achieve these results, known laser eye surgery systems make use of a variety of mechanisms to selectively expose the corneal tissue to the ablative laser energy so as to change the optical characteristics of the eye uniformly throughout the optically used portion of the cornea. Often times, the desired change in shape is effected by selectively removing corneal tissue according to a spherical ablation profile (for example, for treatment of myopia and hyperopia). Cylindrical astigmatism is often treated by selectively removing corneal tissue according to a cylindrical profile, in which the cylinder extends laterally across the optical axis of the eye.

Many patients suffer from optical defects which are not easily treated using known spherical or cylindrical ablation techniques. It has been proposed to treat patients suffering from nonsymmetrical or other types of astigmatism by defining a custom ablation profile. Ophthalmic measurement techniques which may be capable of generating highly accurate topographic information on a particular cornea are now being developed. Unfortunately, integrating these topographic measurements together with new ablation algorithms may take years. In the meantime, patients having irregular corneal defects which significantly limit their vision are in need of treatment today.

In light of the above, it would be desirable to provide improved laser eye surgery devices, systems, and methods. It would be beneficial if these improvements allowed the treatment of irregular corneal defects, particularly if these benefits were available and safe for use in the near-term.

2. Description of the Background Art

The following patents and patent applications may be relevant to the present invention: U.S. Pat. No. 5,683,379, issued Nov. 4, 1997, for "Apparatus for Modifying the Surface of the Eye Through Large Beam Laser Polishing and Method of Controlling the Apparatus", U.S. Pat. No. 4,724,522, issued Feb. 9, 1988, for "Method and Apparatus for Modification of Corneal Refractive Properties", U.S. Pat. No. 5,098,426, issued Mar. 24, 1992, for "Method and Apparatus for Precision Laser Surgery", U.S. Pat. No. 5,290,272, issued Mar. 1, 1994, for "Method for the Joining of Ocular Tissues Using Laser Light", U.S. Pat. No. 5,314,422, issued May 24, 1994, for "Equipment for the Correction of Presbyopia by Remodelling the Corneal Surface by Means of Photo-Ablation", U.S. Pat. No. 5,391,165, issued Feb. 21, 1995, for "System for Scanning a Surgical Laser Beam", U.S. Pat. No. 5,439,462, issued Aug. 8, 1995, for "Apparatus for Removing Cataractous Material", U.S. Pat. No. 5,549,596, issued Aug. 27, 1996, for "Selective Laser Targeting of Pigmented Ocular Cells", U.S. Pat. No. 5,549,597, issued Aug. 27, 1996, for "In Situ Astigmatism Axis Alignment", U.S. Pat. No. 5,556,395, issued Sep. 17, 1996, for "Method and System for Laser Treatment of Refractive Error Using an Offset Image of a Rotatable Mask", U.S. Pat. No. 5,634,919, issued Jun. 3, 1997, for "Correction of Strabismus by Laser-Sculpting of the Cornea", U.S. Pat. No. 5,637,109, issued Jun. 10, 1997, for "Apparatus for Operation on a Cornea Using Laser-Beam", PCT International Application No. PCT/EP95/01287, filed Apr. 7, 1995, for "Method and Apparatus for Providing Precise Location of Points on the Eye", European Patent Application No. 94303256.5, filed May 5, 1994, for "Method and System for Laser Treatment of Refractive Errors Using Offset Imaging", U.S. patent application Ser. No. 09/274,499, filed Mar. 23, 1999, for "Multiple Beam Laser Sculpting System and Method". The full disclosure of these references is hereby incorporated by reference.

SUMMARY OF THE INVENTION

The present invention provides improved laser eye surgery devices, systems, and methods. The invention provides near-term customized ablation capabilities for treatment of corneal irregularities by ablating standard refractive therapy profiles at a position which is offset from the pupillary center. These treatment profiles may, when centered on the eye, be suitable for treatment of standard refractive errors such as myopia, hyperopia, and symmetrical cylindrical astigmatism. By selectively offsetting one or more of these ablation profiles at selected points across the corneal surface, the laser system can reduce refractive errors resulting from corneal irregularities such as irregular astigmatism, corneal steepening in one quadrant, asymmetrical astigmatism, irregularities inadvertently produced by a prior refractive treatment (such as radial keratotomy incisions, a decentered ablation, asymmetric warpage as a result of corneal transplants, penetrating keratoplasty, or the like), granular dystrophy, diffuse, bilateral keratoconus, or the like.

In a first aspect, the invention provides a method for treating an eye of a patient. The eye has a cornea and a pupil, the pupil having a center. The method comprises aligning a laser delivery system with the pupil of the eye. A treatment center on the cornea is designated so that the treatment center is offset laterally (in the X and/or Y direction) from the center of the pupil. A region of the cornea is ablated by directing laser energy according to a therapy profile centered at the treatment center, which may be at some distance from the pupillary center.

The therapy may further comprise selecting the therapy profile from a library including a myopic treatment profile, a hyperopic treatment profile, and a cylindrical treatment profile. These treatment profiles may be scaled for both size and power, and still further therapy profiles may be included in the library. A more complete library may include myopic ablations which are spherical, cylindrical, and/or elliptical in shape; hyperopic ablations which are spherical, cylindrical, and/or provide smooth transition zones; and optionally including therapeutic ablations such as phototherapeutic keratectomy slits and/or phototherapeutic keratectomy circles of variable sizes and having variable transition zones.

Corneal irregularities will often benefit from combinations of two or more therapy profiles centered at different treatment centers on the cornea. By providing a variety of different treatment profiles which can be scaled and selectively offset from each other, often at least partially overlapping on the corneal surface, a wide variety of customized contoured ablations may be effected without having to generate individual customized ablation algorithms to effect the desired overall treatment profile.

The particular profile or profiles applied to a patient's eye will often be identified or planned using a map of the cornea. Elevation maps, such as those which might be produced using wavefront technology now under development, are particularly beneficial for selecting, scaling, and offsetting the therapy profiles over the corneal surface to mitigate the corneal irregularity. Advantageously, it is not necessary to (although it is possible to) link these developmental topography systems to the ablation system to generate customized therapies. Instead, a system operator may select individual ablation size, shape, location, and power based on a topography map, so as to plan the total combined treatment, optionally simulating the effect of the proposed ablation before it is implemented. In fact, while elevation map data results are preferred due to their accuracy and location, depth, and size of irregular corneal features, tangential and/or axial maps may be used independently and advantageously combined to supply the desired information.

In another aspect, the invention provides a system for treating an eye of a patient. The eye has a cornea and pupil with a center. The system comprises a laser producing a laser beam capable of ablating the cornea. Delivery optics are coupled to the laser. Alignment optics are aligned with the delivery optics for maintaining alignment between the laser and the pupil of the eye. An input for designating at least one treatment center is coupled to the delivery optics. The treatment center is offset laterally from the center of the pupil while the pupil of the eye is aligned with the alignment optics.

In a standard symmetrical ablation, alignment optics are aligned with the delivery optics so that the delivered laser beam is coincident and concentric with the alignment reticle. The patient's pupil is generally aligned to the reticle of the alignment optics. If a treatment is desired wherein the treatment beam is not to be centered on the pupil, the operator can specify how far and in what direction the beam is to be displaced from the alignment center. Typically, a controller will direct the optics to deflect the beam laterally so as to effect a treatment profile centered about the designated treatment center. The treatment profile will often be produced by directing numerous individual laser pulses over varying overlapping regions of the cornea. The controller and delivery optics may make use of small spot scanning techniques, large area ablation techniques with variable blocking of the laser energy, and/or overlapping intermediate sized spots which are laterally deflected using mirrors, lenses, or the like. The controller may effect the treatment profiles by moving scanning mechanisms, selecting apertures, varying iris or slot sizes, often according to a treatment table or position calculation algorithm. Regardless, the controller will preferably have and/or make use of a tangible data storage medium with a library of alternative refractive therapies which may be selected and/or scaled individually or in combinations. The library will typically include profiles suitable for treatment of myopia, hyperopia, and cylindrical astigmatism when centered on the optical axis of the eye. By offsetting one or more of these therapies, a wide variety of corneal irregularities may be treated.

BRIEF DESCRIPTION OF THE DRAWINGS

FIG. 10 illustrates therapy profiles and scale parameters included within an exemplary library.

FIGS. 11A and B illustrate data entry screens for selecting, offsetting, scaling, and combining standard ablation profiles to treat corneal irregularities.

DESCRIPTION OF THE SPECIFIC EMBODIMENTS

Figure 1:
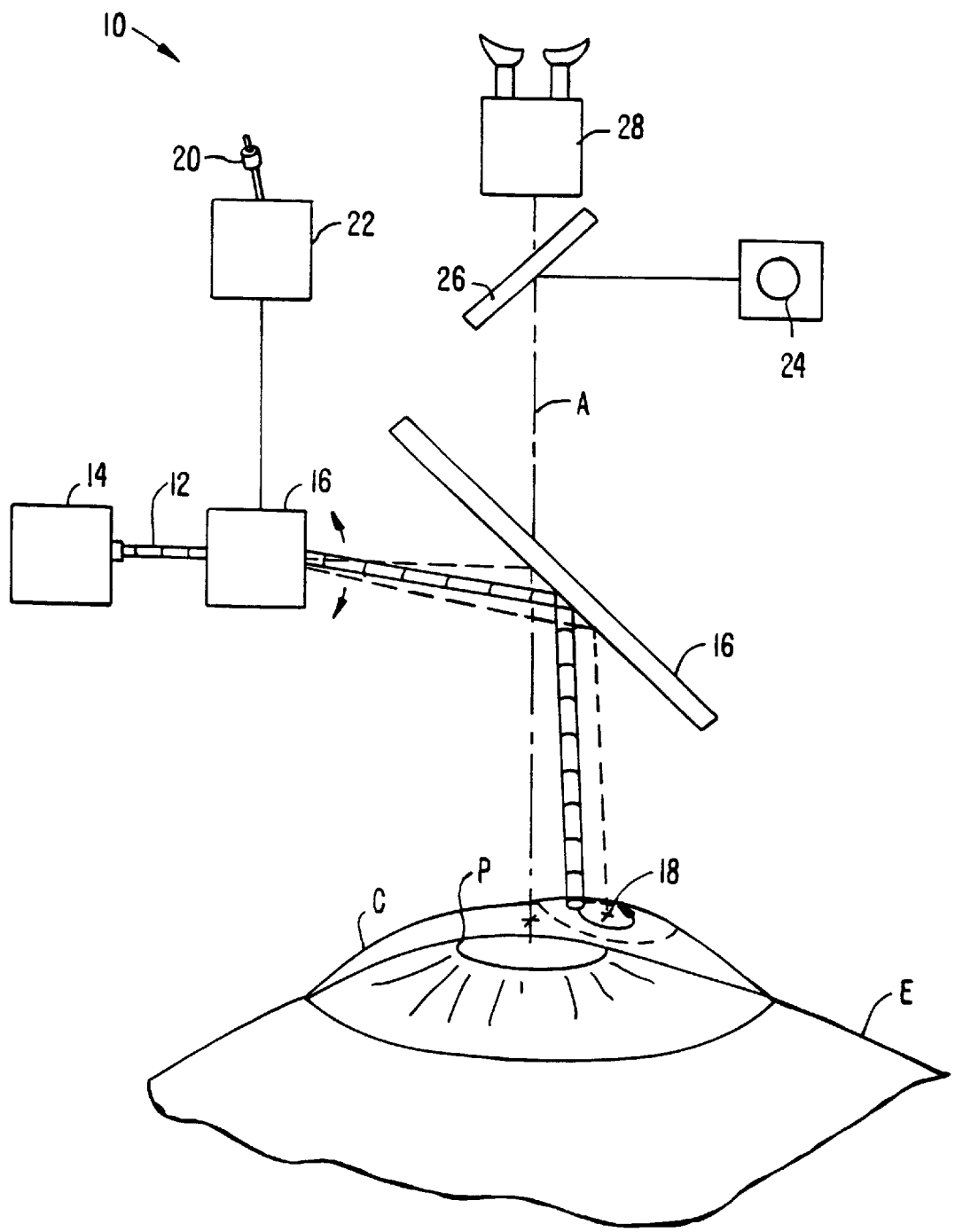
FIG. 1 schematically illustrates a custom ablation system which applies refractive therapy profiles at a location laterally offset from an optical axis of the eye.

Referring now to FIG. 1, a system 10 for treatment of corneal irregularities directs a laser beam 12 from a laser 14 to an eye E having a cornea C. A pupil P has a center defining an optical axis A.

An optical train 16 variably directs laser beam 12 onto the surface of cornea C according to a treatment profile. Rather than treating cornea C with a profile centered about axis A, an operator designates a treatment center 18 which is offset laterally (often described as the X–Y plane) from the center of pupil P.

The operator designates treatment center 18 using an input 20 coupled to controller 22, the input here schematically illustrated as a joystick. The orientation of eye E is stabilized by the patient viewing a fixation target 24 through alignment optics 26. The operator will often direct the ablation procedure while viewing eye E through a microscope 28.

Figure 2:
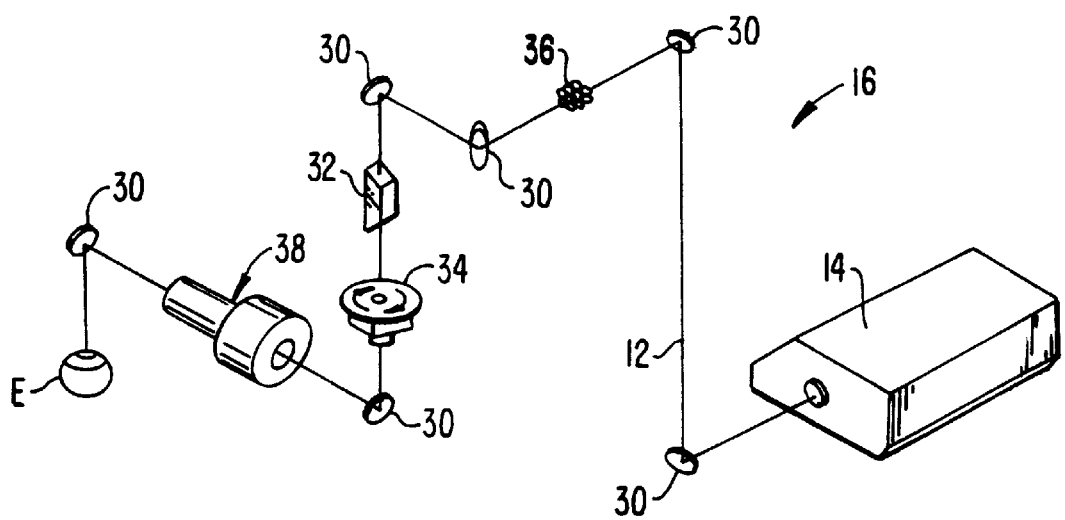
FIGS. 2 and 3 schematically illustrate an optical train for selectively directing a laser beam onto the corneal tissue.

Referring now to FIG. 2, laser delivery optics 16 for directing laser beam 12 at eye E will often include a number of mirrors 30, as well as one or more integrators which may even (or otherwise tailor) the energy distribution across the laser beam. Laser 14 will often comprise an excimer laser or a suitably frequency multiplied solid state laser generating laser energy having a frequency suitable for corneal tissue ablation with minimal thermal damage to the underlying tissue. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193–215 nm) such as those disclosed in U.S. Pat. Nos. 5,144,630, 5,742,626, Borsuztky et al., "Tunable UV Radiation at Short Wavelengths (188–240 nm) Generated by Sum Frequency Mixing in Lithium Borate", Appl. Phys. 61:529–532 (1995), and the like. The laser energy may comprise a beam formed as a series of discreet laser pulses. A variety of alternative lasers might also be used.

Figure 3:
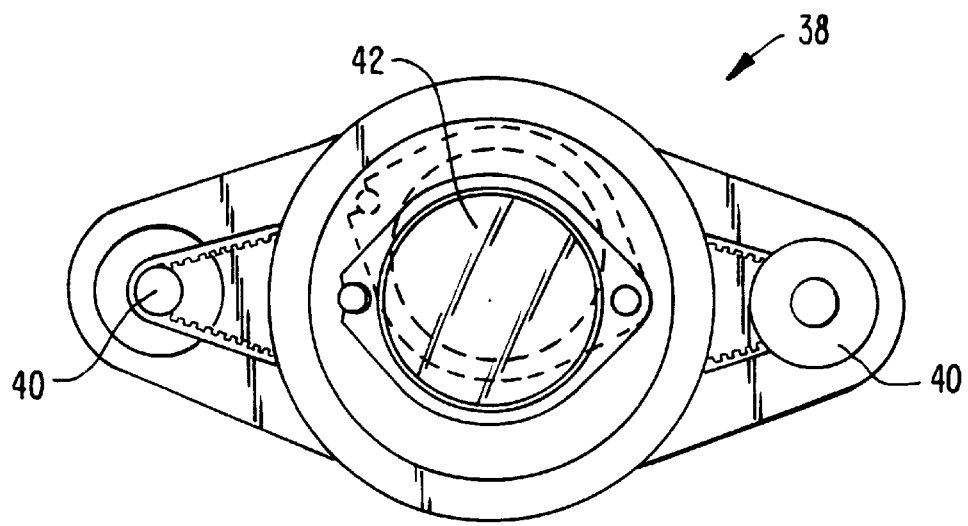

In the exemplary embodiment, a variable aperture 34 changes a diameter and/or slot width to profile laser beam 12, ideally including both a variable diameter iris and a variable width slot. A prism 36 separates laser beam 12 into a plurality of beamlets, which may partially overlap on eye E to smooth edges of the ablation or "crater" from each pulse of the laser beam. Referring now to FIGS. 2 and 3, an offset module 38 includes motors 40 which vary an angular offset of an offset lens 42, and which also change the radial orientation of the offset. Hence, offset module 38 can selectively direct laser beam 12 at a desired lateral region of the cornea. A structure and method for using optical train 16 and offset module 38 are more fully described in co-pending U.S. patent application Ser. No. 08/968,380, entitled "Method and System for Laser Treatment of Refractive Errors Using Offset Imaging" filed Nov. 12, 1997, U.S. patent application Ser. No. 09/185,914, entitled "Method and System for Laser Treatment of Refractive Errors Using Offset Imaging" filed Nov. 4, 1998, and U.S. patent application Ser. No. 09/274,499, entitled "Multiple Beam Laser Sculpting System and Method", filed Mar. 23, 1999, the full disclosures of which are incorporated herein by reference.

Figure 4:
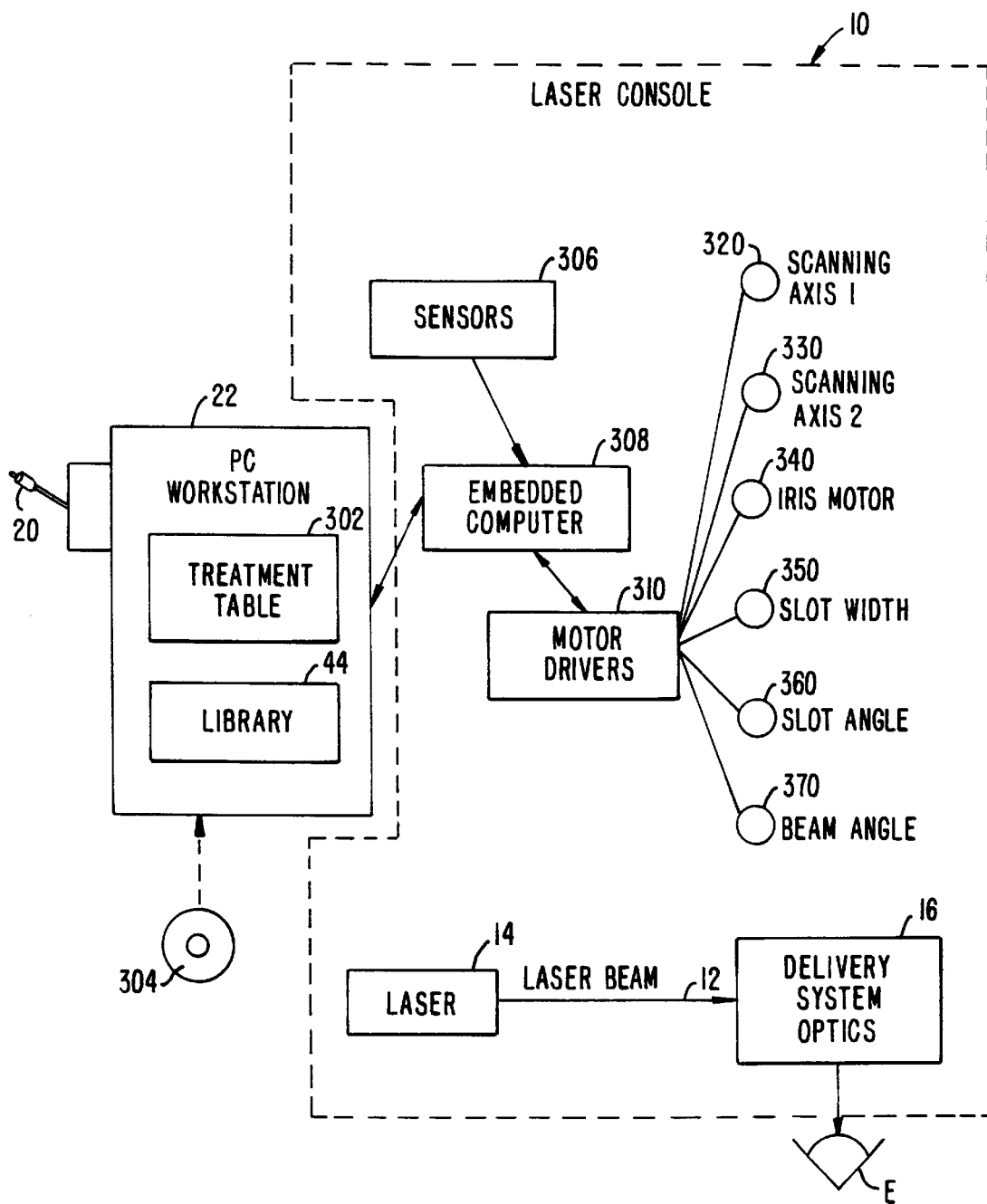
FIG. 4 is a function block diagram illustrating the control in scanning architecture of the customized ablation system of FIG. 1.
Figure 5:
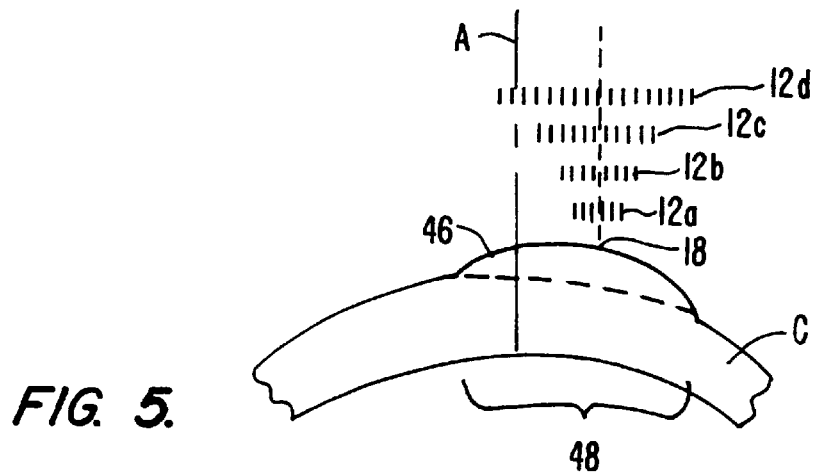
FIGS. 5 through 8 schematically illustrate the use of off-center refractive ablation profiles for treatment of corneal irregularities.

Referring now to FIG. 4, elements of a VISX Star S2™ excimer laser system, as commercially available from VISX, Incorporated of Santa Clara, Calif., are schematically illustrated as modified for use according to the principles of the present invention. A computer control system 22 enables precise control of laser system 10 to sculpt a surface shape specified in a laser treatment table 302. A controller 22, which generally comprises a PC workstation, makes use of a computer program stored on a tangible media 304 to generate treatment table 302. An embedded computer 308 within laser system 10 is in electronic communication with the PC workstation, and may thereby comprise a portion of the overall controller. Alternatively, a PC workstation may be embedded in the laser system and function as both the embedded computer and PC workstation for directing the ophthalmic surgery.

Embedded computer 308 is in electronic communication with a plurality of sensors 306 and a plurality of motor drivers 310. The motor drivers are coupled to the controller to vary the position and configuration of many of the optical components of the delivery optics 16 according to treatment table 302. For example, first and second scanning axis 320, 330 control the position of the offset lens to move the beamlets over the surface of the cornea. Iris motor 340 controls the diameter of the overall beam, and in some cases, the length of light transmitted through a variable width slot. Similarly slot width driver 350 controls the width of the variable slot. Slot angle driver 360 controls rotation of the slot about its axis. Beam angle driver 370 controls rotation of the beam, while laser 14 is pulsed to generate the laser beam 12 after the various optical elements have been positioned to create a desired crater on eye E. Treatment table 302 may comprise a listing of all of the desired craters to be combined so as to effect a treatment therapy.

For customizing ablations to treat irregular corneas, controller 22 will preferably include library 44 having a number of different photorefractive and/or phototherapeutic ablation profiles. These ablation profiles will often be used for treatment of spherical and/or cylindrical refractive errors of the eye by coaxially locating treatment center 18 at the center of pupil P. To treat irregular corneas, these same ablation profiles may be directed to laterally offset treatment center 18 using input device 20. Conveniently, the controller can modify the treatment table to offset the ablation profile by adjusting each ablation coordinate with the desired offset.

While the input device 20 is here schematically illustrated as a joystick, it should be understood that a variety of input mechanisms may be used. Suitable offset input mechanisms may include trackballs, touch screens, or a wide variety of alternative pointing devices. Still further alternative input mechanisms include keypads, data transmission mechanisms such as an ethernet, intranet, internet, a modem, or the like. These or other input mechanisms may be used to identify an offset treatment center 18 which is offset laterally from the center of the pupil of the eye.

Figure 6:
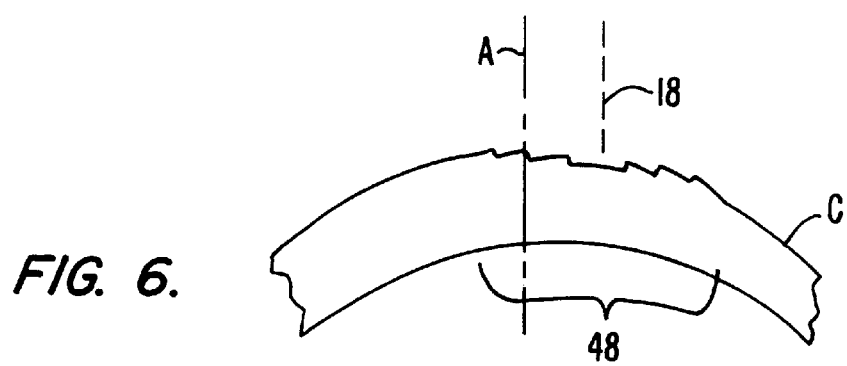

The use of standard ablation profiles to treat an irregular cornea can be understood with reference to FIGS. 5 through 8. Cornea C in FIG. 6A features a protruding irregularity 46 of corneal tissue which is offset laterally from the optical axis A. To treat this condition, a series of laser pulses (schematically illustrated as pulses 12a–d) of gradually varying size are directed over a treatment region 48 which is centered at offset treatment center 18. Such gradually varying diameter pulse patterns could be applied coaxially with the optical axis to flatten a central portion of the cornea and treat myopia. However, by offsetting this same treatment profile laterally, protruding corneal tissue 46 may be ablated so as to resculpt the cornea to a more sphercial shape, as illustrated in FIG. 6.

Figure 7:
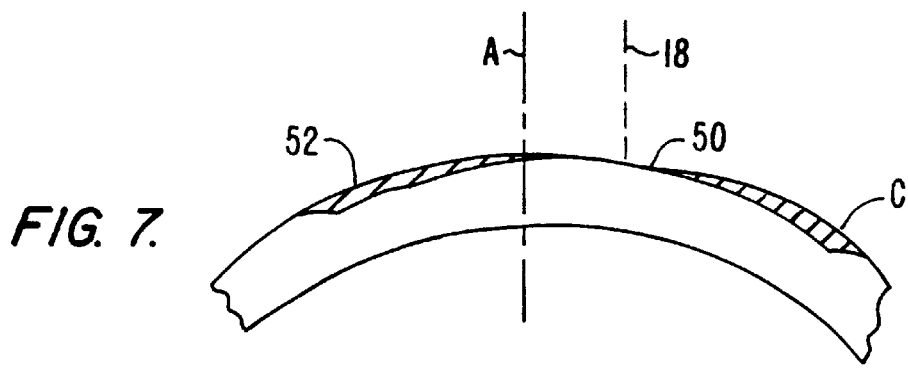

Alternative standard photorefractive therapies may also be applied, as illustrated in FIG. 7. Cornea C here initially has a flat region 50 having insufficient curvature. A hyperopia ablation profile 52, which is most often used to increase the curvature of the central cornea, is here offset laterally so as to be centered at offset center 18 so as to increase the curvature of the corneal surface about flat region 50.

Figure 8:
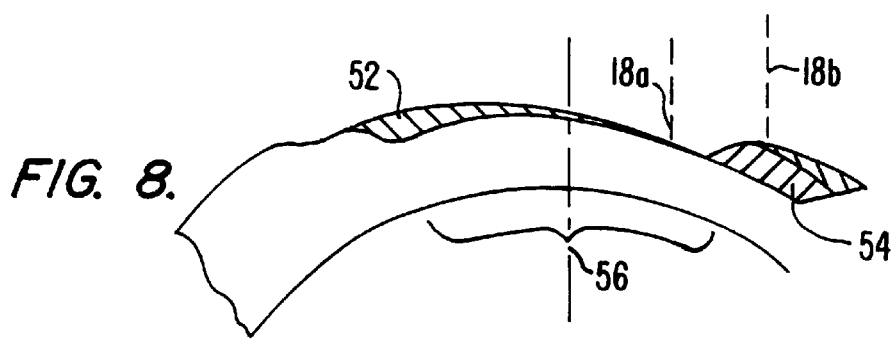

Treatment of a previously decentered ablation is schematically illustrated in FIG. 8 using first a hyperopia ablation profile 52 centered at offset treatment center 1 8a, followed by a myopia ablation profile 54 center at another offset treatment center 18b so as to decrease the irregularity of the cornea throughout an optically used region 56. It should be understood that the examples illustrated in FIGS. 6A through 8 are schematic, that the offset treatment center may be offset in both X and Y directions, and that the multiple treatment centers will often be radially offset from each other. Additionally, it should be understood that the refractive treatment profiles will often be scaled in size and power. Algorithms and techniques for generating the therapeutic ablation profiles by combining individual ablation pulse craters are described in the patent literature listed hereinabove.

Figure 9:
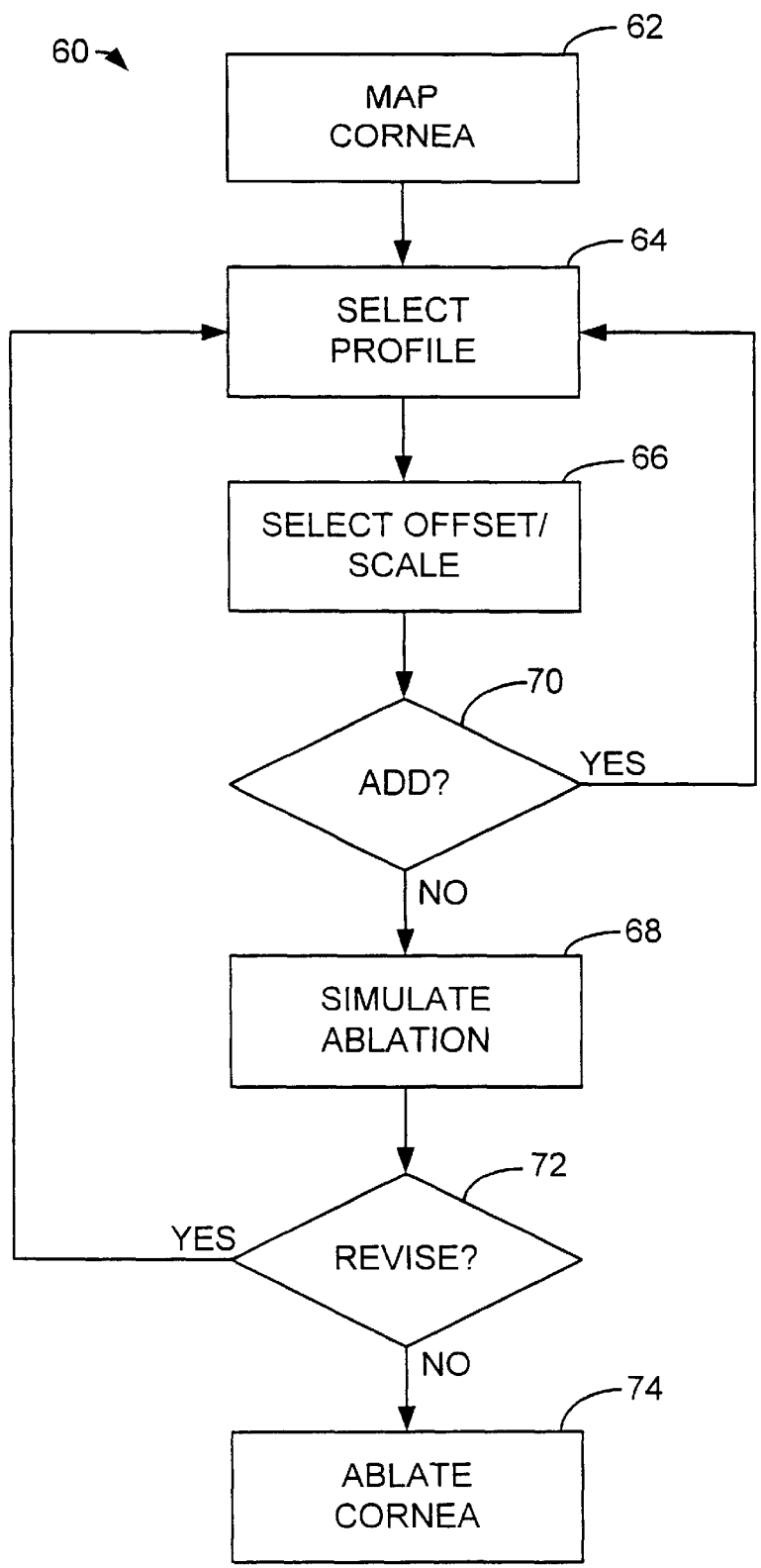
FIG. 9 is a flowchart illustrating steps for treatment of a cornea irregularity using offset ablation profiles.

A flow chart 60 illustrating the individual steps for developing a custom ablation strategy is illustrated in FIG. 9. Preferably, a map of the cornea will be prepared 62 using any of a wide variety of commercially available ophthalmic measurement techniques. Particularly advantageous topography measurements may be available using wavefront technology now being developed. As described hereinbelow, corneal maps based on the axial curvature or tangential curvature of the cornea may also be used independently, and/or these maps may be combined to back calculate micron elevation data.

Based on the corneal map 62, a standard ablation profile is selected 64 with a proposed scale and offset 66. Where only a single ablation profile may be sufficient, the proposed ablation may then be simulated 68, with the resulting corneal characteristics presented to verify the proposed ablation parameters. In many cases, one or more additional ablation profiles may be added 70, or where appropriate, deleted from a previous ablation plan before the total ablation procedure is simulated. If the ablation simulation 68 indicates further refinement in the ablation plan would be beneficial, the plan may be revised by adding and/or subtracting ablation profiles, varying the offset and scale of individual ablation profiles, or the like. If no further revision 72 is desired, the combined profile ablation plan may be implemented to ablate the cornea 74.

An exemplary library of myopic, hyperopic, and therapeutic ablation profiles is listed in FIG. 10. The standard ablation profiles may be scaled in both dimensions and power, with the maximum and minimum scaling parameters being as listed. In general, photorefractive profiles refer to both myopic profiles (or surfaces) and hyperopic profiles (or surfaces) as listed, while therapeutic ablation profiles refer to the corresponding shapes listed below the "therapeutic surface" heading.

The exemplary data input screens for selection of ablation profiles, designating offsets and scales, and adding or subtracting profiles are illustrated in FIGS. 11A and 11B. As illustrated in FIG. 11A, a plurality of ablations may be entered for sequential and/or simultaneous ablation with individually designated offsets and scaling. Entry of the parameters for a particular ablation profile such as the offsets 80, size 82, and power 84 may be performed using a standard Windows™-type data entry system including a mouse or other pointing device and/or a keyboard.

Figure 12A:
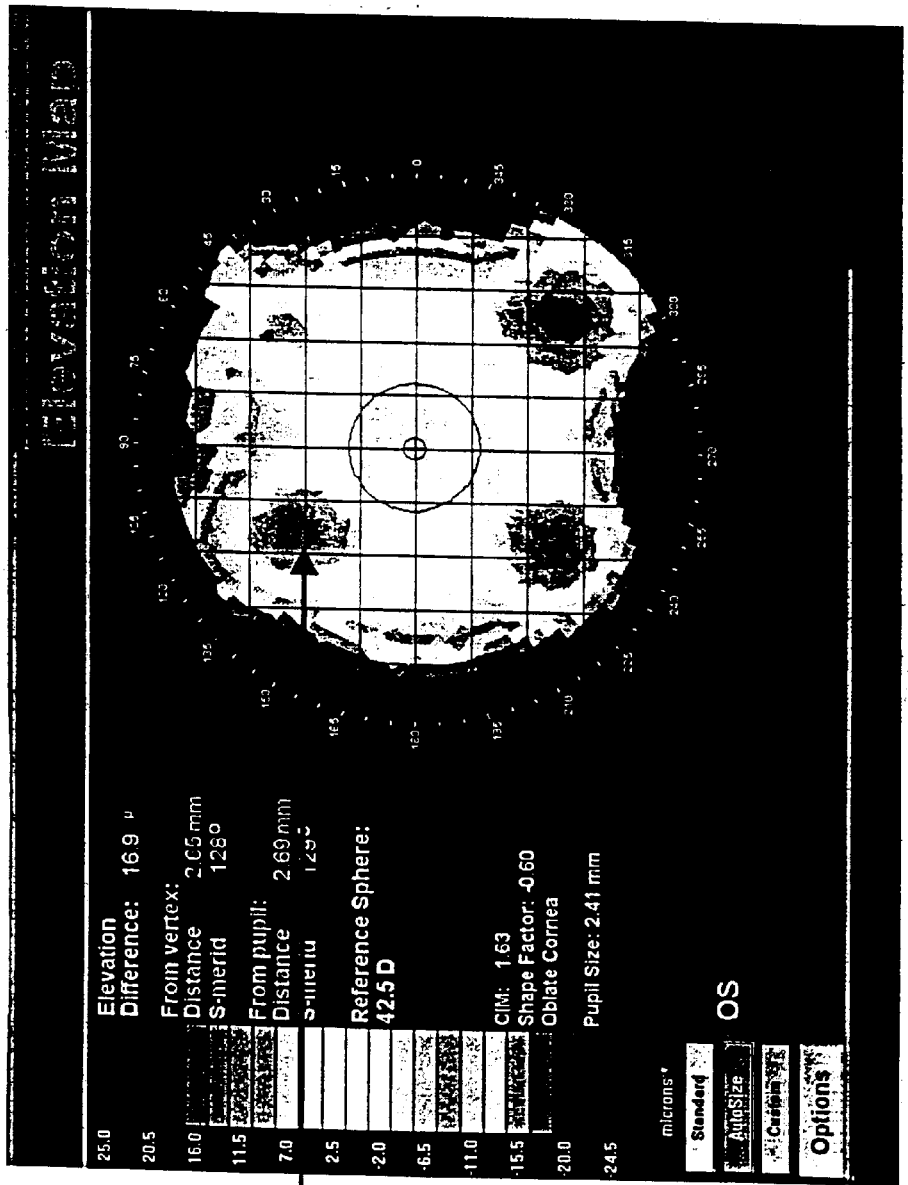
FIGS. 12A through C schematically illustrate alternative maps for planning a custom combined ablation.
Figure 12B:
Figure 12C:
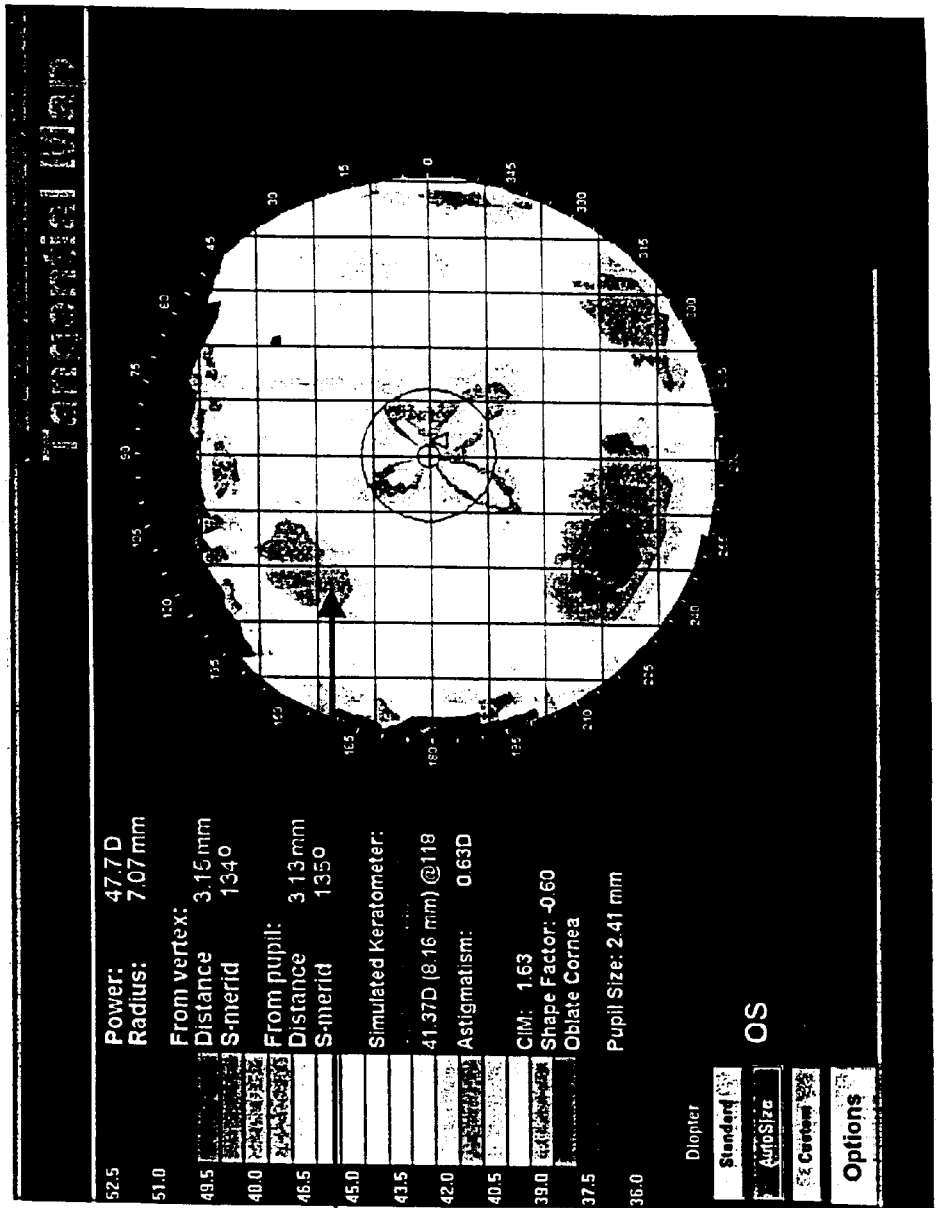

Referring now to FIGS. 12A through C, elevation maps are particularly advantageous for generating the desired ablation plan, as they accurately indicate shape, location, depth, and size or irregular corneal features, as illustrated in FIG. 12A. While axial curvature maps (as illustrated in FIG. 12B) provide good power values, they can be less accurate regarding the location and size of irregularities. Tangential maps such as that illustrated in FIG. 12C provide good location and size information, but may be less accurate regarding specific power values. Advantageously, axial and tangential maps can be combined so as to "back calculate" elevation data, thereby significantly facilitating the planning of a custom ablation profile.

Advantageously, a proposed ablation plan may be entered into the computer based on a visual review of the corneal map. The plan may be tailored to treat asymmetrical astigmatism, inferior corneal steepening, corneal dystrophy, decentered ablations, errors inadvertently induced by prior refractive procedures, or a wide variety of other corneal irregularities. Proposed treatments may be generated to generally improved uncorrected visual acuity and/or optimize best corrected visual acuity for a particular patient. More generally, the tailored plan may enhance the overall quality of vision and reduce visual aberrations caused by irregularities.

Advantageously, it is not necessary to link a topography system directly to an ablation system or ablation algorithm for generation of a treatment plan. Individual ablation profile settings and combinations may be controlled by the system operator, thereby providing near-term capabilities for patient's suffering from these visual defects. Alternatively, it may be advantageous to eventually link the topography information directly to the ablation profile planning computer. Hence, the selection, offset, and scaling of the ablation profiles may be performed either manually and/or automatically. Regardless, the corneal map and specific ablation mechanism may employ a variety of different structures within the scope of the present invention.

Figure 13:
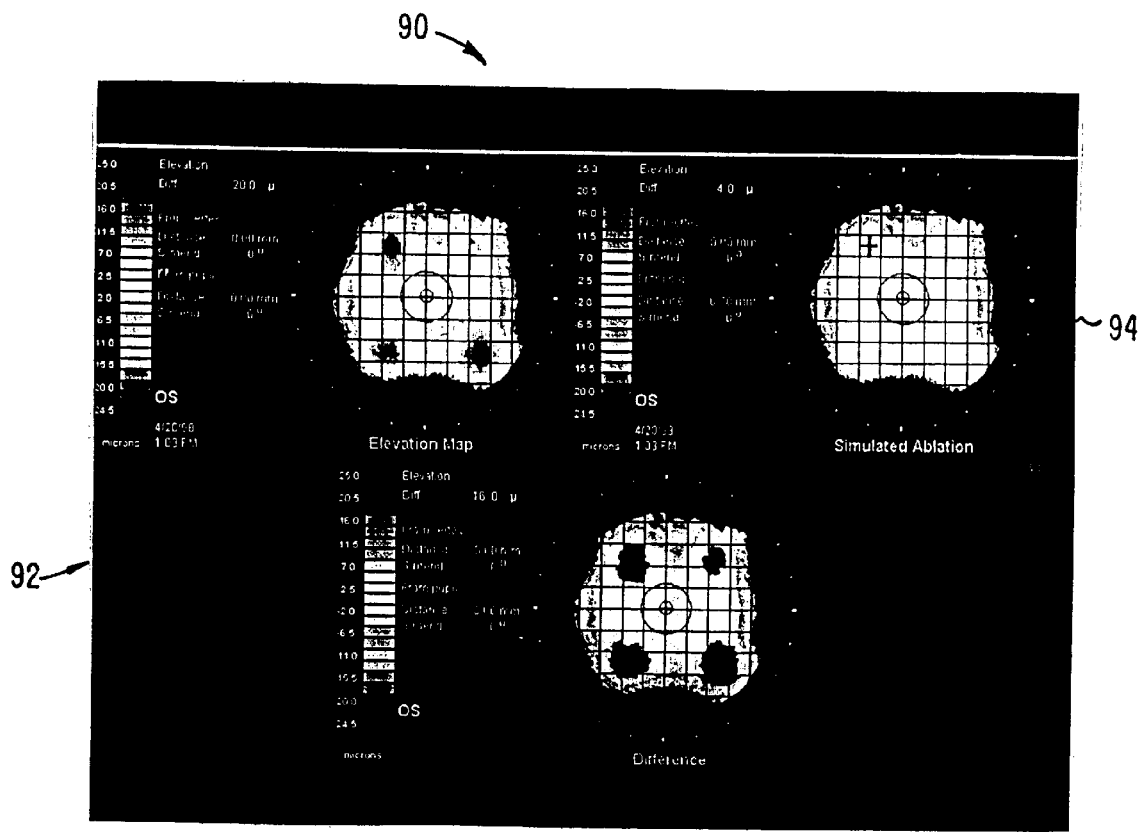
FIG. 13 illustrates information displayed for planning and simulating a combined ablation to verify the proposed combination of ablation profiles prior to treatment of the eye.

Referring now to FIG. 13, after (or optionally during) selection and scaling of the individual ablation profiles based on a corneal map 90, the computer may mathematically simulate the total ablation to determine a change in the corneal map 92 and a resulting simulated ablated cornea 94, before actually removing corneal tissue. This allows the physician or other system operator to compare before and after maps of the cornea so as to visualize the results, and to investigate a variety of alternative treatment plans prior to the actual ablation.

While the exemplary embodiment has been described in some detail, by way of example and for clarity of understanding, a variety of adaptations, changes, and modifications will be obvious to those of skill in the art. Hence, the scope of the present invention is limited solely by the appended claims.

What is claimed is:

1. A method for treating an eye of a patient, the eye having a cornea and a pupil, the pupil having a center, the method comprising:

aligning a laser delivery system with the pupil of the eye;

designating a first treatment center on the cornea, the first treatment center being offset laterally from the center of the pupil;

selecting a first therapy profile from a library of therapy profiles for regular refractive errors, the therapy profile comprising a member of a group consisting of a myopic treatment profile, a hyperopic treatment profile, and a cylindrical astigmatism treatment profile; and ablating a region of the cornea by directing laser energy from the aligned laser delivery system according to the first therapy profile centered at the first treatment center.

2. The method of claim 1, further comprising:

selecting a second therapy profile from the library of therapies;

designating a second treatment center on the cornea, the second treatment center being offset from the first treatment center and from the center of the pupil;

scaling the first therapy profile and the second therapy profile; and, ablating a second region of the cornea with the second therapy profile centered about the second treatment center so that the therapy profiles of the ablated regions are offset from each other and from the center of the pupil.

3. The method of claim 1, wherein the ablating step is performed so as to mitigate a refractive error of the eye selected from the group consisting of irregular astigmatism, corneal steepening in one quadrant, and asymmetrical astigmatism.

4. The method of claim 1, further comprising:

measuring the eye to generate a map of the eye;

selecting the therapy profile in response to the map from a library of standard therapies; and selecting the offset in response to the map so as to mitigate an irregular refractive error of the eye.

5. The method of claim 4, wherein the measuring step generates an elevation map of the eye.

6. A method for treating an eye of a patient, the eye having a cornea and a pupil, the pupil having a center, the method comprising:

aligning a laser delivery system with the pupil of the eye;

designating a treatment center on the cornea, the treatment center being offset laterally from the center of the pupil; and ablating a region of the cornea by directing laser energy from the aligned laser delivery system according to a therapy profile centered at the treatment center, wherein the ablating step spherically ablates the cornea about the treatment center so as to aspherically resculpt the cornea about the center of the pupils.

7. The method of claim 6, wherein the spherical resculpting step comprises decreasing a curvature of the cornea adjacent the treatment center according to a myopic ablation profile.

8. The method of claim 6, wherein the spherical resculpting step comprises increasing a curvature of the cornea adjacent the treatment center according to a hyperopic ablation profile.

9. A method for treating an eye of a patient, the eye having a cornea and a pupil, the pupil having a center, the method comprising:

aligning a laser delivery system with the pupil of the eye;

designating a treatment center on the cornea, the treatment center being offset laterally from the center of the pupil; and ablating a region of the cornea by directing laser energy from the aligned laser delivery system according to a therapy profile centered at the treatment center, wherein the ablating step cylindrically resculpts the cornea along a cylindrical axis, wherein the center of the pupil is offset laterally from the cylindrical axis.

10. A method for treating an eye of a patient, the eye having a cornea and a pupil, the pupil having a center, the method comprising:

aligning a laser delivery system with the pupil of the eye;

designating a treatment center on the cornea, the treatment center being offset laterally from the center of the pupil; and ablating a region of the cornea by directing laser energy from the aligned laser delivery system according to a therapy profile centered at the treatment center, wherein the ablating step mitigates a refractive error inadvertently produced by a prior treatment to the eye.

11. The method of claim 10, wherein the prior treatment comprises a prior ablation, and wherein the prior ablation was offset laterally from the center of the pupil.

* * * * *